United States Patent [19]
Krueger et al.

[11] Patent Number: 5,735,894
[45] Date of Patent: Apr. 7, 1998

[54] HOLDER FOR HEART VALVE PROSTHESIS

[75] Inventors: Kurt D. Krueger, Stacy; Guy Vanney, Blaine, both of Minn.

[73] Assignee: St. Jude Medical, Inc., St. Paul, Minn.

[21] Appl. No.: 653,633

[22] Filed: May 24, 1996

Related U.S. Application Data

[63] Continuation-in-part of Ser. No. 449,145, May 24, 1995, Pat. No. 5,578,076.

[51] Int. Cl.$^6$ .................................................. A61F 2/24
[52] U.S. Cl. .................................................. 623/2; 623/900
[58] Field of Search .................................. 623/2, 900, 66; 606/1

[56] References Cited

U.S. PATENT DOCUMENTS

| | | | |
|---|---|---|---|
| 3,860,005 | 1/1975 | Anderson et al. | 623/2 |
| 4,185,636 | 1/1980 | Gabbay et al. | 128/334 R |
| 4,683,883 | 8/1987 | Martin | 623/2 |
| 4,755,181 | 7/1988 | Igoe | 623/2 |
| 4,865,600 | 9/1989 | Carpentier et al. | 623/2 |
| 5,443,502 | 8/1995 | Cavdillo et al. | 623/2 |
| 5,480,425 | 1/1996 | Ogilive | 623/2 |
| 5,578,076 | 11/1996 | Krueger et al. | 623/2 |
| 5,582,607 | 12/1996 | Lackman | 623/2 |

FOREIGN PATENT DOCUMENTS 1690739  11/1991  U.S.S.R. ............... 623/2

*Primary Examiner*—John G. Weiss
*Assistant Examiner*—Bruce E. Snow
*Attorney, Agent, or Firm*—Hallie A. Finucane, Esq.; Westman, Champlin & Kelly, P.A.

[57] ABSTRACT

A device for engaging a heart valve prosthesis during implantation includes a heart valve prosthesis holder. The holder includes a distal engaging surface adapted for engaging the heart valve prosthesis. The distal engaging surface carries a compliant member which maintains an occluder of the heart valve in a closed position during implantation.

21 Claims, 17 Drawing Sheets

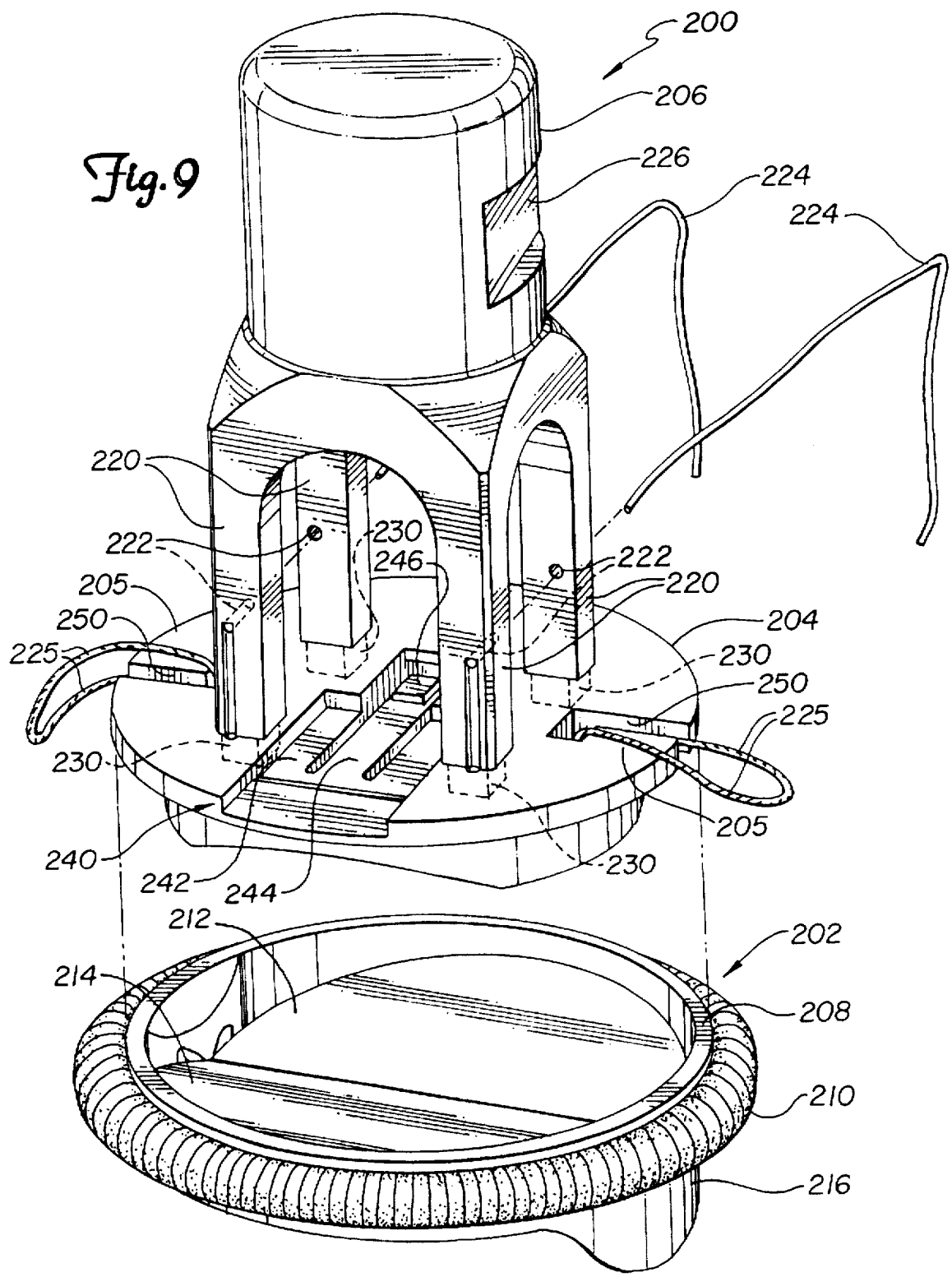

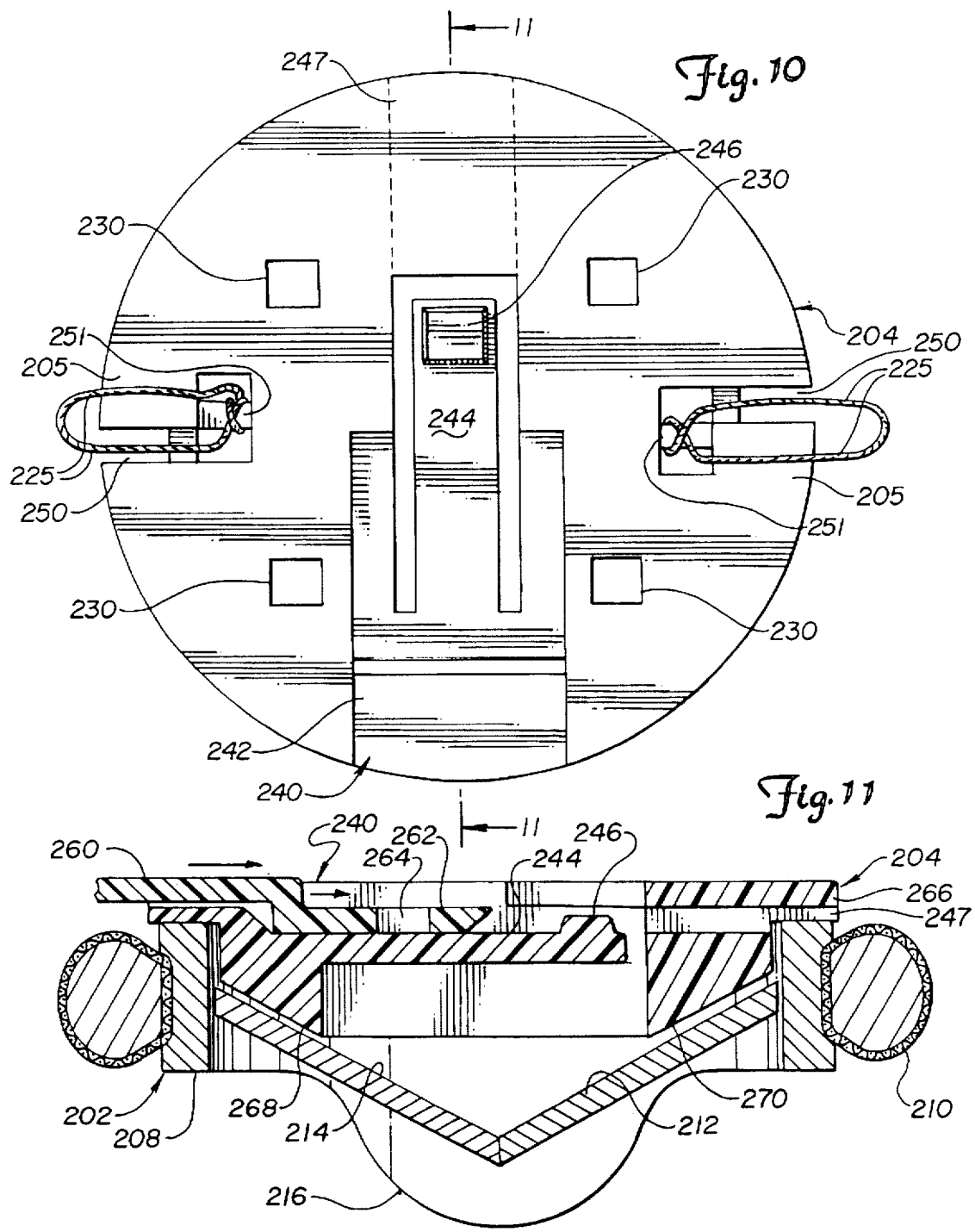

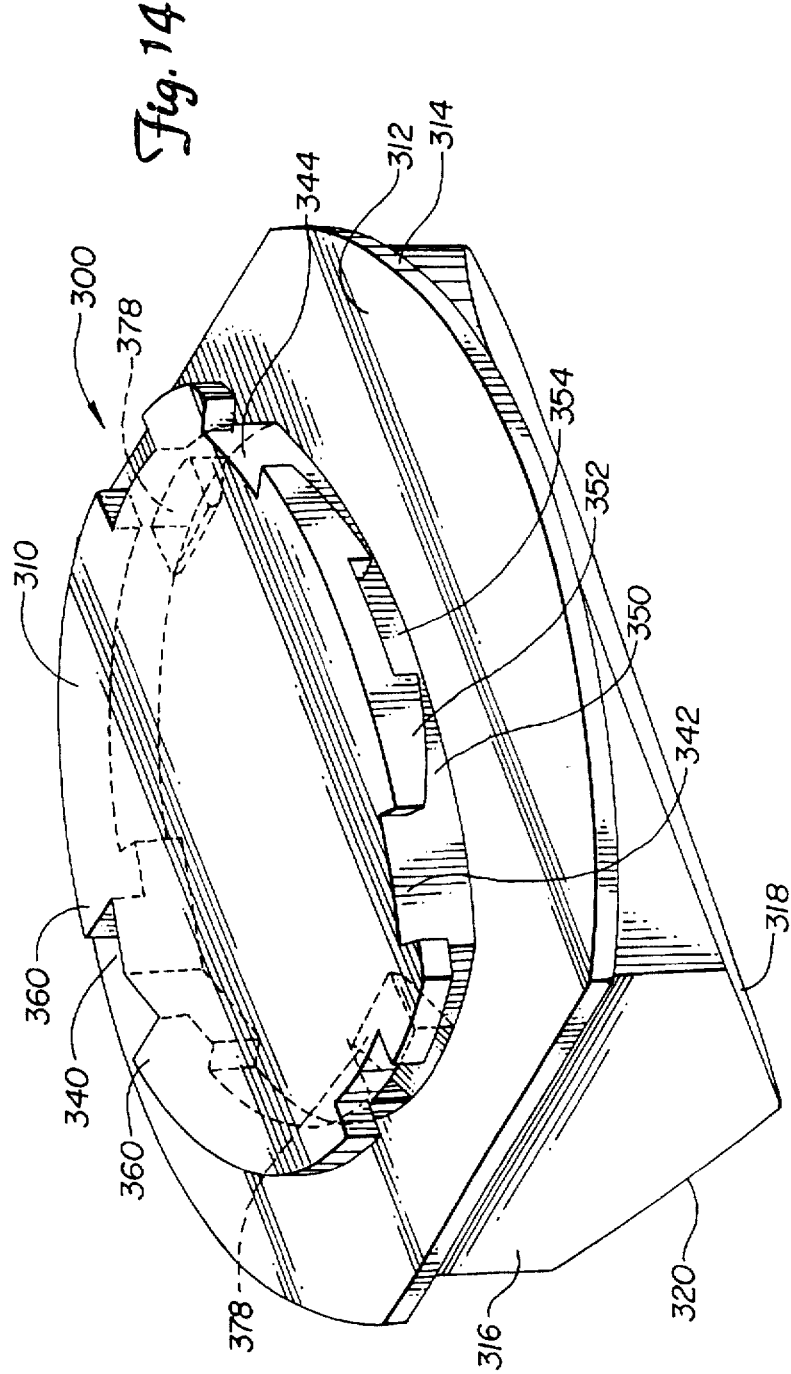
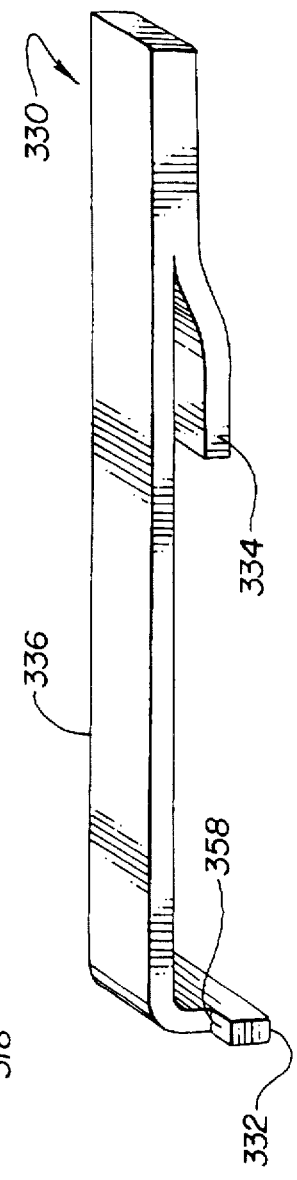

HOLDER FOR HEART VALVE PROSTHESIS

FIELD OF THE INVENTION

This is a Continuation-In-Part application of U.S. Ser. No. 08/449,145, filed May 24, 1995 U.S. Pat No 5,578,076.

The present invention relates to devices for implanting heart valve prostheses. More specifically, the invention relates to a low profile holder for holding a heart valve prosthesis during implantation.

BACKGROUND OF THE INVENTION

Holders for holding heart valve prostheses during implantation are known. They are used for positioning, holding, supporting and presenting the valve during surgery. U.S. Pat. No. 3,828,787, issued Aug. 13, 1974, to Anderson et al., entitled COLLET FOR HOLDING HEART VALVE, shows a heart valve holder carried on a distal end of an elongated handle. U.S. Pat. No. 4,932,965, issued Jun. 12, 1990, to Phillips, entitled ARTIFICIAL VALVE, AND NEEDLE AND SUTURE HOLDER AND METHOD OF USING SAME, shows another heart valve holder in which the valve is held against distal ends of a pair of elongated legs during implantation.

Typically, heart valve replacement surgery is an involved procedure in which a sternotomy or thoracotomy is performed and the chest cavity of the patient must be widely opened to provide access to the patient's heart. This provides a surgeon with direct unobstructed access to the heart. However, this procedure requires a prolonged period to recover from the trauma suffered to the upper torso.

Recently, a procedure has been developed wherein open heart surgery is performed through trocars placed in small incisions between two ribs of the patient. This is described in international Publication No. WO 94/18881, entitled METHOD FOR PERFORMING THORASCOPIC CARDIAC BYPASS PROCEDURES. In this procedures elongated tools are used to operate on the heart through the trocars. As discussed in Publication No. 94/18881, this procedure can be used during heart valve replacement.

The trocar requires minimal rib spreading and does not involve the significant chest trauma associated with traditional open heart surgery. One advantage of this procedure is that the recovery period can be reduced significantly. Unfortunately, mechanical heart valves and the associated assembly used for implantation are large relative to the trocar and are difficult to fit therethrough. Further, the delicate valve occluders protrude from the prosthesis and may be damaged during insertion through the narrow trocar.

SUMMARY OF THE INVENTION

A device for engaging a heart valve prosthesis during implantation includes a heart valve prosthesis holder. The heart valve prosthesis has an annulus with a substantially annular aperture therein and at least one occluder movable between an open position and a closed position. The holder has a proximal surface and a distal engaging surface adapted for engaging the heart valve prosthesis. A compliant member is provided to maintain the occluder in the closed position. In one embodiment, this is a suture. The same suture may be used to attach the holder to the heart valve prosthesis.

BRIEF DESCRIPTION OF THE DRAWINGS

FIG. 9 is an exploded perspective view of another embodiment.

FIG. 10 is a top plan view of a valve holder shown in FIG. 9.

FIG. 11 is a cross-sectional view of a valve holder and heart valve of FIG. 10.

FIG. 14 is a top perspective view of a holder in accordance with another embodiment.

FIG. 15 is a plan view of a handle adapted for attachment to the holder of FIG. 14.

DETAILED DESCRIPTION OF THE PREFERRED EMBODIMENTS

The invention relates to a device which is a low profile heart valve holder used to position a heart valve prosthesis during implantation. Preferably, this implantation is through minimally invasive surgery such as when performed through a small trocar between two ribs of the patient near the patient's arm. The holder and valve are carried at the distal end of a handle which extends perpendicular to an axis of the valve annulus during insertion through the trocar. For purposes of this description of the invention, the holder will be described generally with regard to its use with a bi-occluder mechanical heart valve which has an annulus with a substantially annular aperture. Such a heart valve prosthesis is available from St. Jude Medical, Inc. of St. Paul, Minn. However, the invention is applicable to other types of heart valves as well.

Figure 1:
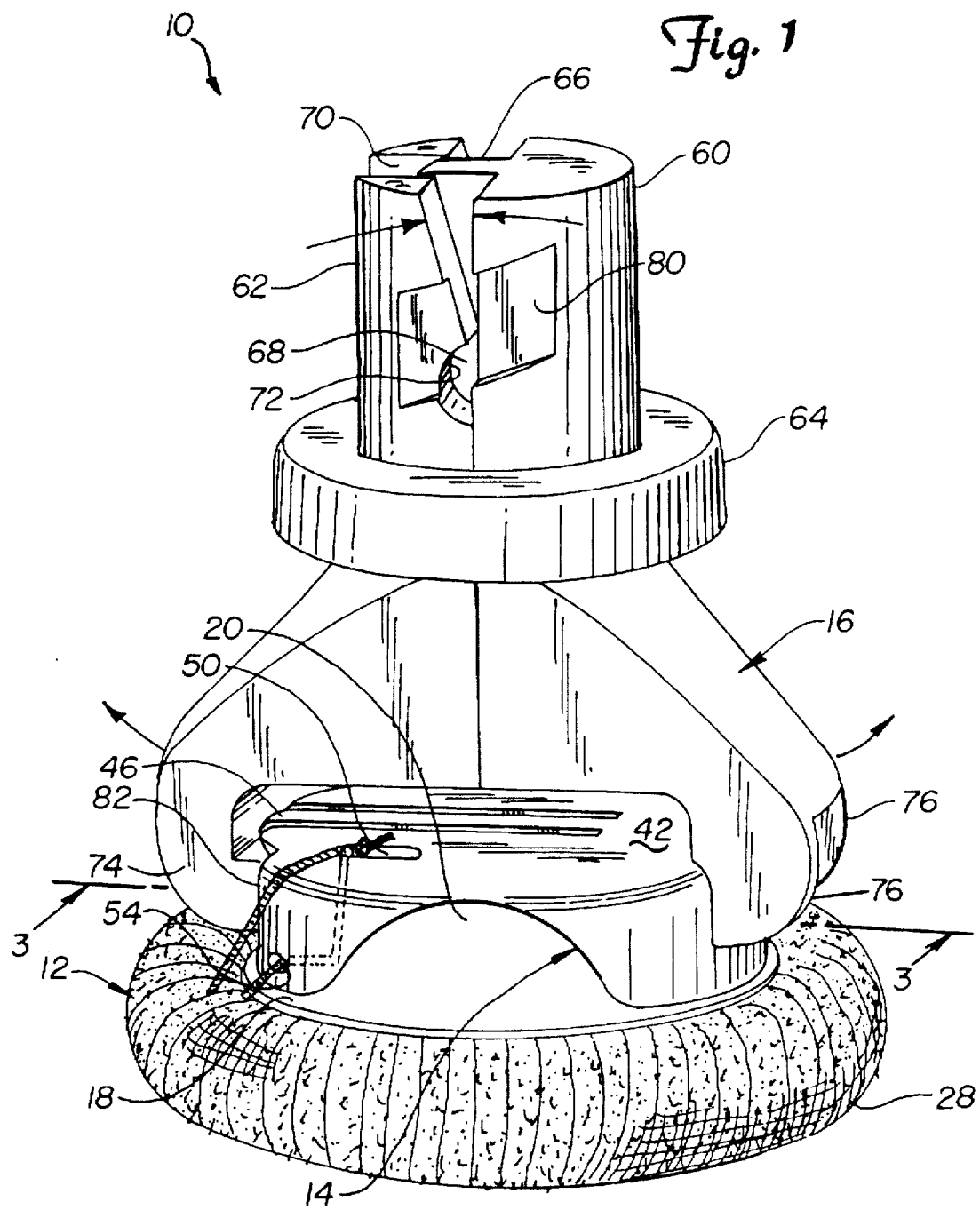
FIG. 1 is as perspective view of an assembly including a low profile mitral valve holder in accordance with one embodiment.
Figure 2:
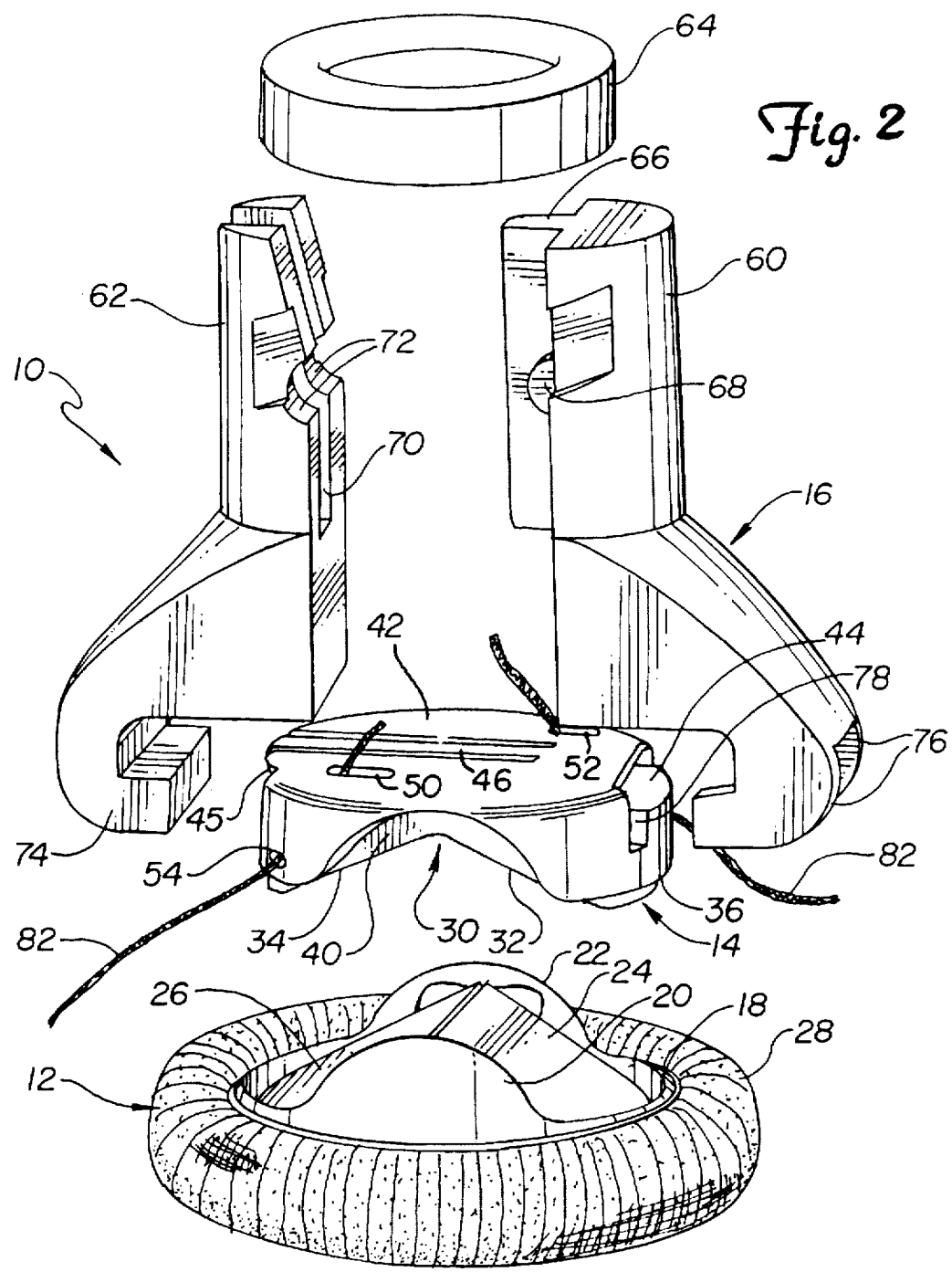
FIG. 2 is an exploded perspective view of the assembly of FIG. 1.

FIG. 1 is a perspective view and FIG. 2 is an exploded perspective view, respectively, of an assembly 10 which includes mitral heart valve prosthesis 12, heart valve holder 14 and hanger 16. Valve 12 includes valve orifice 18 having occluder pivot guards 20 and 22 which carry occluders 24 and 26. A suture cuff 28 surrounds the outer radius of orifice 18.

Figure 3:
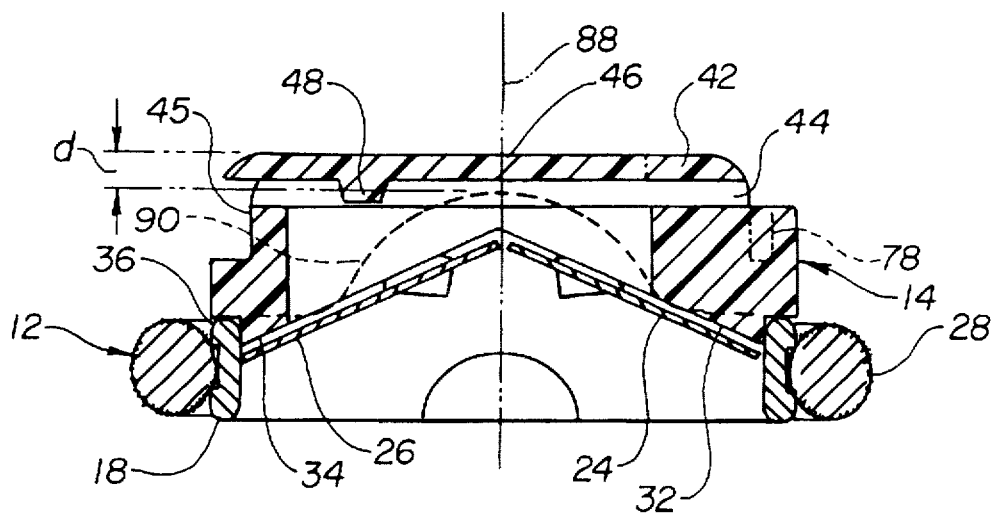
FIG. 3 is a cross-sectional view of the valve holder and valve of FIG. 1 taken along line 3—3.

Holder 14 includes distal surface 30 which provides occluder conforming surfaces 32 and 34 adapted for receiving a proximal side of valve 12. A radial lip 36 extends around the outer circumference of distal surface 30 and conforms to valve orifice 18. Holder 14 includes pivot guard receiving portion 40 adapted for receiving pivot guard 20 (and 22). Holder proximal surface 42 is a planar surface which is substantially parallel with the annulus of valve 12 and perpendicular to the axis 88 of valve 12, as shown in FIG. 3. Surface 42 is positioned proximate pivot guards 20 and 22 to provide an overall low profile to holder 14 as viewed from the side. Surface 42 overlies slot 44 and includes cantilever arm 46 which carries tab 48 (shown in FIG. 3). Surface 42 includes suture holes 50, 52 and the outer radius of holder 14 includes suture holes 54.

Hanger 16 includes holder stems 60 and 62 and collar 64 which holds stems 60 and 62 together when hanger 16 is assembled onto holder 14. Tab 66 extends outwardly from stem 60 adjacent pivot 68. Stem includes slot 70 for receiving tab 66 and pivot receptacle 72 for receiving pivot 68. Leg 74 of stem 62 fits in slot 45 of holder 14 and legs 76 of stem 60 fit in downward extensions 78 of slot 44. Hanger 16 is adapted for suspending holder 14 and valve 12 at notch 80 in packaging (not shown) during transportation and prior to implantation. Holder 14 is removed from hanger 16 by removing collar 64 from stems 60 and 62 such that stems 60 and 62 rotate about pivot 68 as shown by the arrows in FIG. 1. Holder 14 is secured to valve 12 by sutures 82 which extend through holes 50 and 54 of holder 14 and through cuff 28 of valve 12.

FIG. 3 is a cross-sectional view of valve 12 and valve holder 14 taken along a plane parallel with the axis 88 of valve 12 along line 3—3 in FIG. 1. Dashed line 90 in FIG. 3 indicates the position of the most proximal surface of valve 12. As shown in FIG. 3, the distance between proximal surface 42 of holder 14 and proximal surface 90 of valve 12 is designed to be relatively small. Further, surfaces 32 and 34 of holder 14 maintain occluders 24 and 26 in a closed position such that they do not protrude from valve 12. This configuration provides a significantly lower profile for the valve/holder assembly than in typical prior art designs. By providing a reduced profile, heart valve 12 is more easily inserted into a patient through a trocar between the ribs or other small opening in a patient. Further, occluders 24 and 26 are protected by valve orifice 18 during implantation and do not extend below valve 12. This prevents occluders 24 and 26 from being damaged as heart valve 12 is inserted through the trocar.

Figure 4:
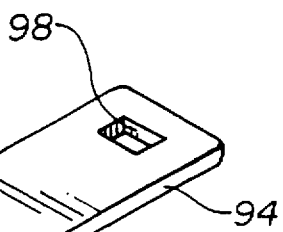
FIG. 4 is a perspective view of a handle for attachment to the holder shown in FIGS. 1 through 3.

FIG. 4 is a perspective view of handle 91 which includes elongated grip 92 coupled to flat distal end portion 94. Distal portion 94 includes opening. Handle 91 is adapted to couple to valve holder 14 by insertion into slot 44. Tab 48 is forced into opening 98 of handle 91 by spring loaded arm 46, thereby releasably securing handle 91 to holder 14. Handle 91 is disengaged by lifting arm 46 while removing distal portion 94 from slot 44.

During implantation, the surgeon removes assembly 10 from the packaging (not shown). Hanger 16 is removed from holder 14 by removing collar 64 and squeezing the proximal end of hanger 16 together. This causes legs 74, 76 to pivot about pivot 68 thereby freeing holder 14. Distal end 94 of handle 91 is inserted into slot 44 and locked into place by tab 48 in opening 98. This may be done before removing hanger 16 from packaging or before removing holder 14 from hanger 16. Occluders 24 and 26 are protected within orifice 18 during insertion. The valve 12 is inserted through the trocar and is secured to the heart tissue annulus. After valve 12 is secured to the tissue annulus of the heart, holder 14 is then removed by cutting sutures 82 and removing handle 91 and holder 14 from the patient.

Figure 5:
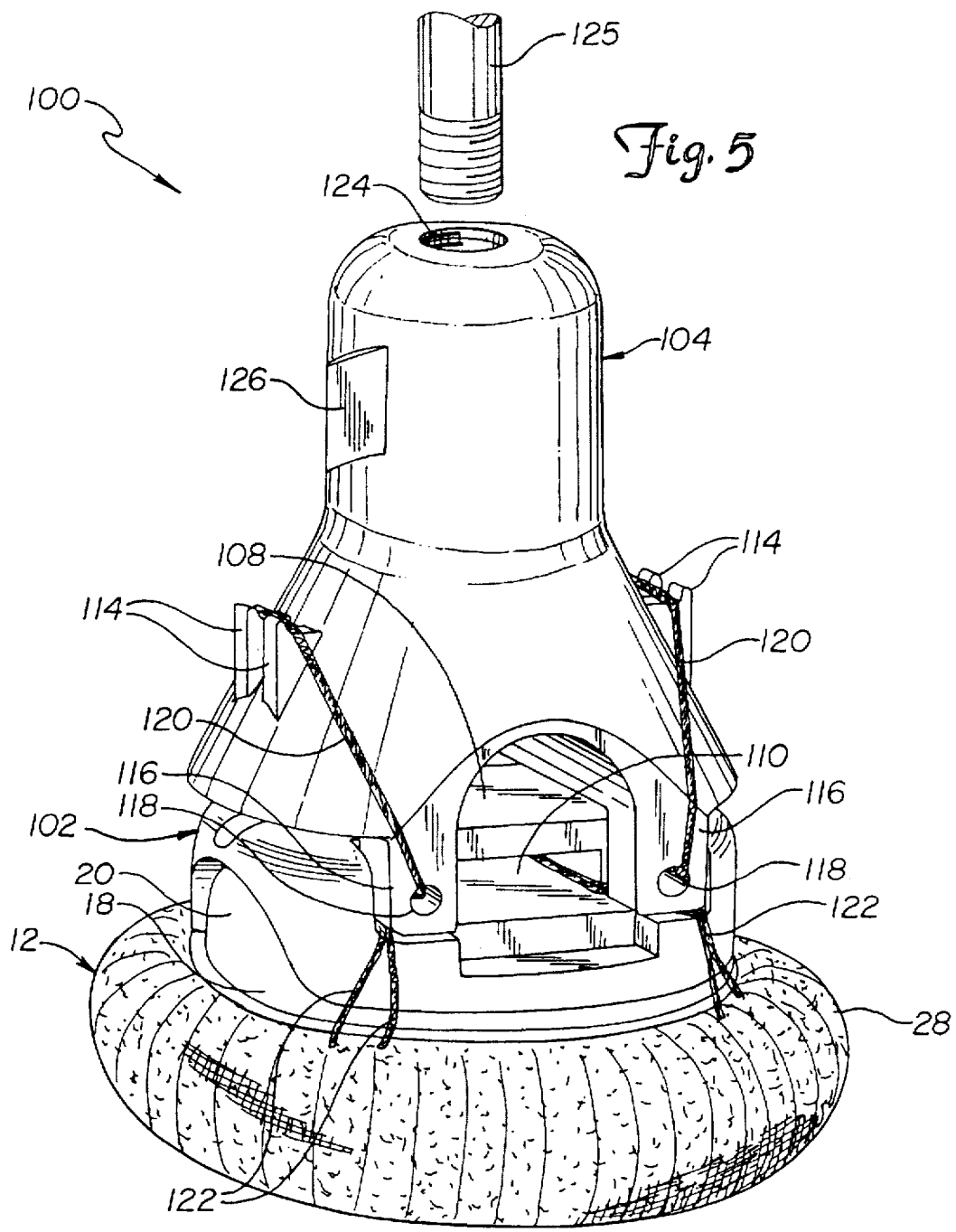
FIG. 5 is a perspective view of an assembly including a valve holder in accordance with another embodiment.
Figure 6:
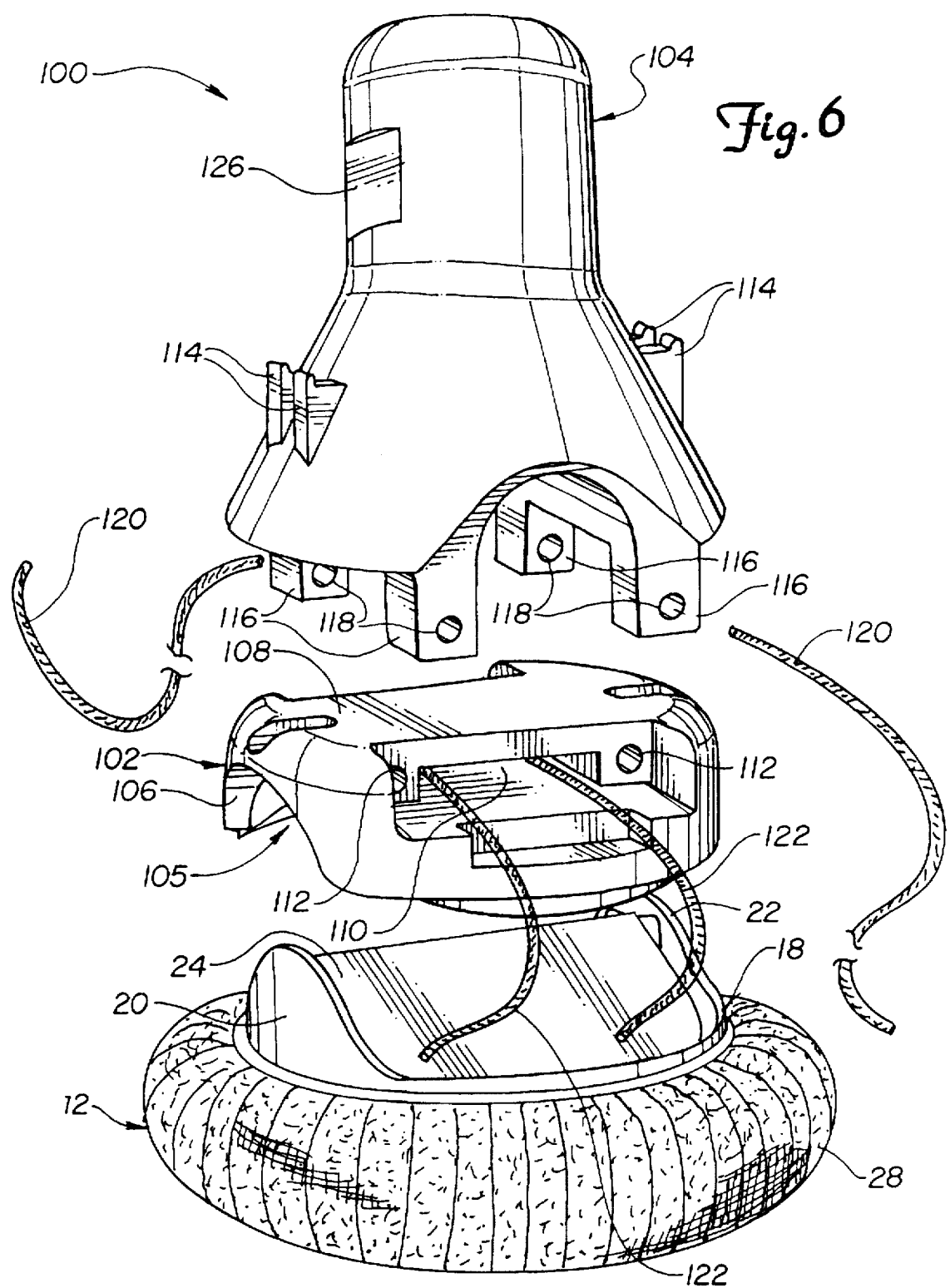
FIG. 6 is an exploded perspective view of the assembly of FIG. 5.

FIGS. 5 and 6 show a perspective view and an exploded perspective view, respectively, of assembly 100 in accordance with another embodiment. Assembly 100 includes holder 102 coupled to valve 12 supported by hanger 104 in the packaging (not shown). A distal engaging surface 105 of holder 102 is similar to surface 30 shown for holder 14 in FIGS. 1 through 3. Holder 102 includes pivot guard receiving portions 106 and proximal surface 108. A slot 10 and suture openings 112 extend through holder 102 perpendicular to the axis of valve 12.

Hanger 104 includes suture shoulders 114 and legs 116 having suture openings 118. Sutures 120 extend through holes 118 of hanger 104 and through holes 112 of holder 102 thereby securing hanger 104 to holder 102. Sutures 122 extend through holes 112 of holder 102 and through cuff 28 of valve 12 thereby securing holder 102 to valve 12. Hanger 104 includes threaded receptacle 124 and notch 126. Notch 126 is used to suspend hanger 104 from packaging (not shown) during transportation prior to implantation of valve 12. Threaded receptacle 124 is optionally used to receive a threaded handle 125 to facilitate removal of assembly 100 prior to implantation.

Assembly 100 is used in a manner similar to that described for assembly 10. The surgeon removes the assembly from the packaging (not shown). A handle is inserted into slot 110. Alternatively, the handle may be inserted into assembly 100 before removing assembly 100 from the package. Sutures 120 are cut such that holder 102 may be removed from hanger 104. The implantation procedure proceeds as described above. After valve 12 has been sutured to the patient's heart, sutures 122 are cut and holder 102 is removed.

Figure 7:
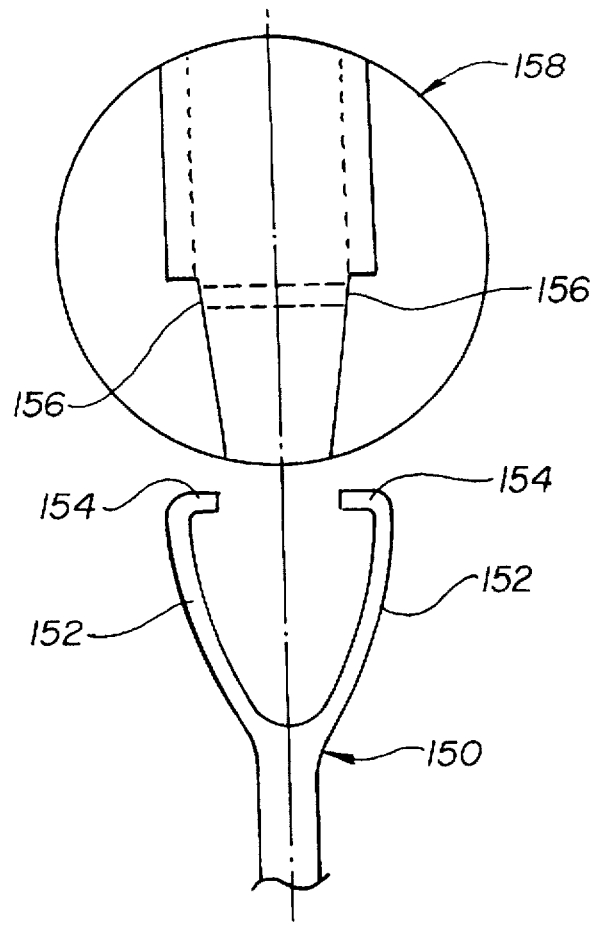
FIG. 7 is a top plan view of a handle and holder in accordance with one embodiment.
Figure 8:
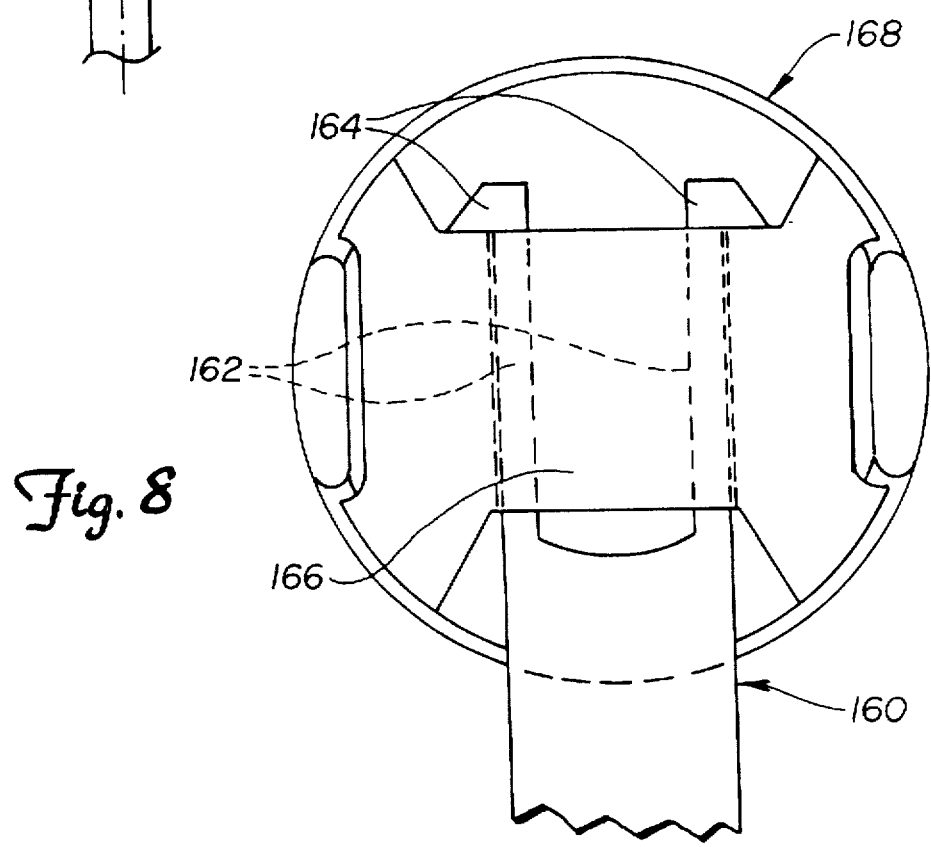
FIG. 8 is a top plan view of a holder and handle in accordance with another embodiment.

FIGS. 7 and 8 are top plan views showing two additional embodiments for attaching the handle to the low profile holders described herein. In FIG. 7, handle 150 includes distal legs 152 each having a tip 154. Openings 156 are provided in holder 158. Openings 156 receive tips 154 such that handle 150 is secured to holder 158. Handle 150 is attached by urging tips 154 toward openings 156 until they engage openings 156. Handle 150 can be removed by spreading tips 150 in an outward direction to disengage openings 156. As shown in FIG. 7, handle 150 is substantially perpendicular to the axis of holder 158 but can pivot relative to holder 158 in opening 156 such that handle 150 is substantially coaxial with the axis of valve 12.

FIG. 8 shows another embodiment in which a handle 160 includes legs 162 each carrying a tab 164. Legs 162 are received in slot 166 of holder 168, as shown in FIG. 8. Tabs 164 lock handle 160 into holder 168 as handle 160 is inserted into slot 166. Removal is by squeezing tabs 164 together.

FIG. 9 is a perspective exploded view of assembly 200 in accordance with another embodiment. Assembly 200 is adapted for use with aortic heart valve prosthesis 202 and includes holder 204 and hanger 206. Aortic valve 202 includes valve orifice 208, cuff 210, occluders 212 and 214 protected by occluder pivot guard 216. Hanger 206 includes hanger legs 220 having suture holes 222 to receive sutures 224. Hanger 206 includes notch 226 adapted for being held in packaging (not shown).

Holder 204 includes hanger leg receptacles 230 adapted for receiving hanger legs 220 of hanger 206. Hanger 206 is attached to holder 204 with sutures 224 which extend through holes 222 and holder 204. Holder 204 attaches to valve 202 with sutures 225, shown in more detail in FIG. 10. Holder 204 includes handle receptacle 240 which includes recessed area 242 and cantilever 244 which carries tab 246. Holder 204 is attached to valve 202 by passing a suture 225 through cuff 210. One portion of suture 225 lies within groove 250 and the other portion of suture 225 lies on holder proximal surface 205. The ends of suture 225 are then wrapped around protrusion 251 within groove 250 and knotted. The recessed suture opening reduces the likelihood that a suture is unintentionally severed by the surgeon.

FIG. 10 is a top plan view of low profile aortic valve holder 204. The plan view of FIG. 10 shows suture grooves 250 which are recessed in holder 204 and adapted for receiving sutures 225. The recessed suture grooves 250 provide a further reduction in the profile of holder 204. Holder 204 includes opening 247 which is provided for manufacture using injection molding techniques.

Figure 12:
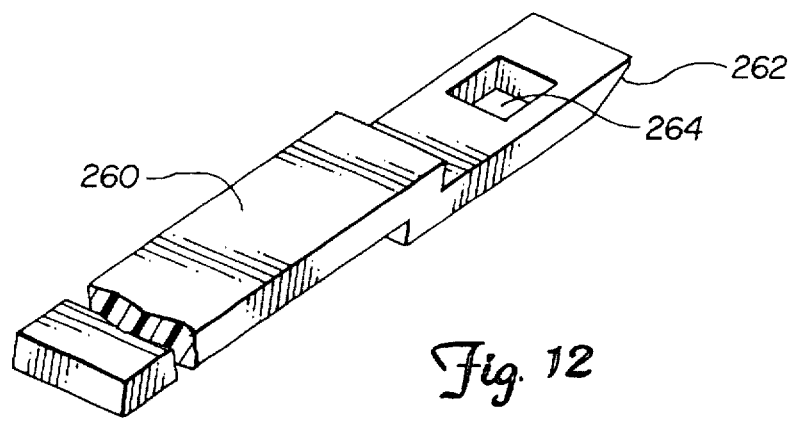
FIG. 12 is a perspective view of a handle shown in cross section in FIG. 11.

FIG. 11 is a cross-sectional view of holder 204, taken along the line labeled 11—11 in FIG. 10, shown prior to operational engagement with valve 202. FIG. 11 also shows handle 260 partially in receptacle 240 and prior to engagement of tab 246 into square hole 264 in the handle. Handle 260 is attached by insertion of end 262 into receptacle 240. With sufficient force, handle 260 may be pulled from receptacle 240. FIG. 12 is a perspective view of handle 260. Handle 260 includes distal end 262 having opening 264. The tip of distal end 262 is beveled to push tab 246 downward as distal end 262 is slid along tab 244 after insertion into opening 240 so that tab 246 is received in opening 264, thereby locking handle 260 to holder 204. As shown in FIG. 11, holder 204 includes lip 266 which extends around valve orifice 208. The distal side of holder 204 is adapted for interfacing with the proximal side of valve 202 and includes occluder engaging surfaces 268 and 270 which are positioned adjacent occluders 214 and 212, respectively. A minimal gap is maintained between occluders 214 and 212 and surfaces 268 and 270 to prevent the occluders from being damaged. However, surfaces 268 and 270 are shaped generally to retain occluders 214 and 212 in a closed position. As discussed above, this helps maintain a low profile for holder 204 and valve 202.

Figure 13:
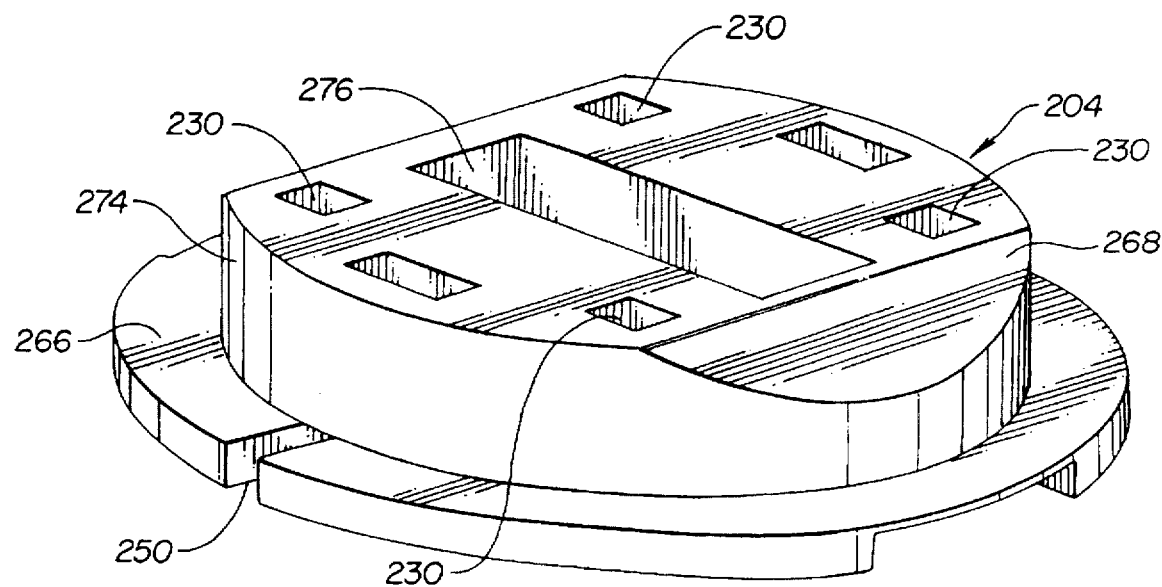
FIG. 13 is a bottom plan view of the holder of FIGS. 10 and 11.

FIG. 13 is a perspective view showing the distal side of valve holder 204. FIG. 13 clearly shows lip 266 which engages valve orifice 208. Generally, the only portion of holder 204 which extends above valve orifice 208 is lip 266. The main body portion 274 of holder 204 is carried within valve orifice 208, as shown in FIG. 11.

FIG. 14 is a perspective view of aortic valve holder 300 for use with valve 202 in accordance with another embodiment. FIG. 14 shows the proximal side of holder 300 which includes attachment (locking) ring 310 carried on upper surface 312 and which includes lip 314. Lip 314 is adapted for engagement with valve orifice 208, shown in FIG. 11. Holder 300 includes main body portion 316 which is received within valve orifice 208. Occluder engaging surfaces 318 and 320 are adapted for engaging occluders 214 and 212, as shown in FIG. 11.

Attachment ring 310 is adapted for attachment to handle 330, shown in FIG. 15. Handle 330 includes distal locking element 332 and proximal locking element 334. Elements 332 and 334 are supported between elongated member 336.

Figure 16:
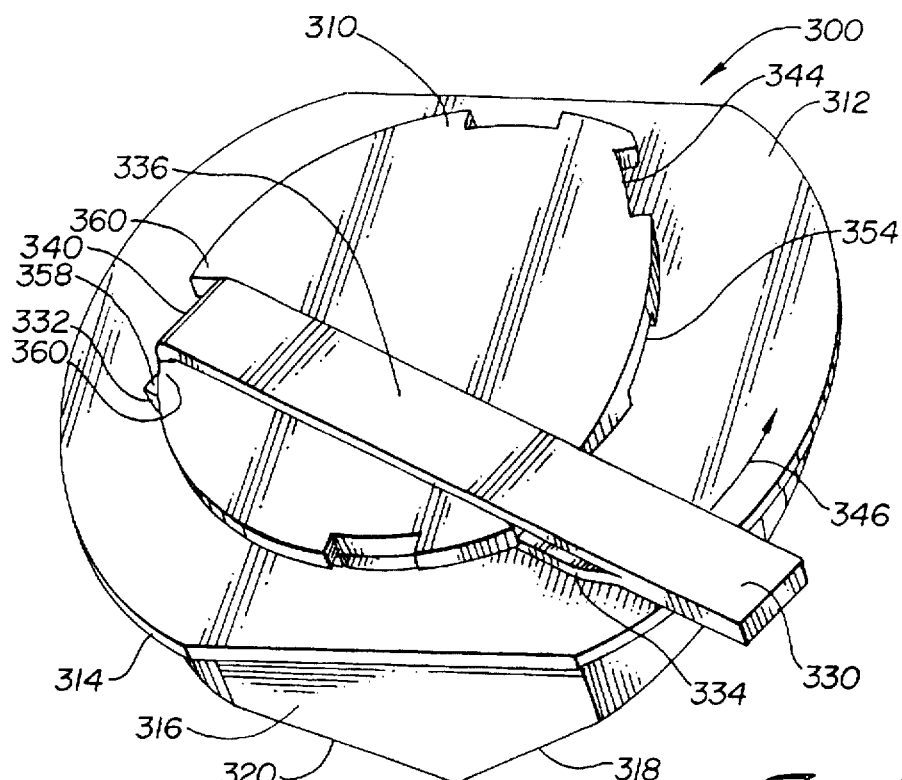
FIGS. 16 and 17 are top perspective views showing attachment of the handle of FIG. 15 to the holder of FIG. 14.
Figure 17:
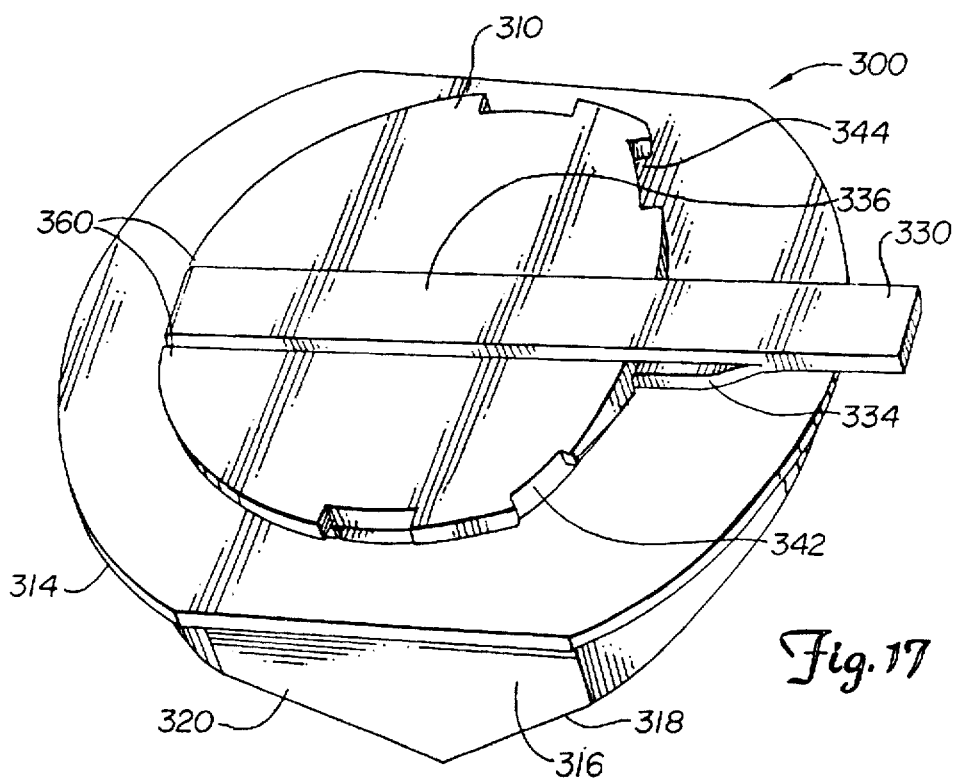

FIGS. 16 and 17 are perspective views showing the steps of locking handle 330 to holder 300. As shown in FIG. 16, distal locking member 332 is placed in distal receptacle 340 while proximal locking member 334 is placed through opening 342 of attachment ring 310 so it is positioned below the lead-in end of ramp 352 (FIG. 14). Opening 344 is similar to opening 342. Handle 330 is then moved in the direction shown by arrow 346 in FIG. 16 to the position shown in FIG. 17. This causes proximal locking member 334 to slide through groove 350, shown in FIG. 14, under and along ramp 352. As handle 330 completes movement to the position shown in FIG. 17, proximal locking member 334 resiliently snaps into locking recess 354 thereby locking handle 330 in position. Note that distal tab 358 is locked under lip 360 of locking ring 310. Thus, both distal locking member 332 and proximal locking member 334 of handle 330 are securely fastened to locking ring 310. This provides two solid points of attachment positioned on opposite sides of the annulus of valve 202. Handle 330 is removed by spreading locking member 334 outwardly such that locking recess 354 is disengaged and handle 330 may be rotated and removed in a manner opposite to that described above.

Figure 18:
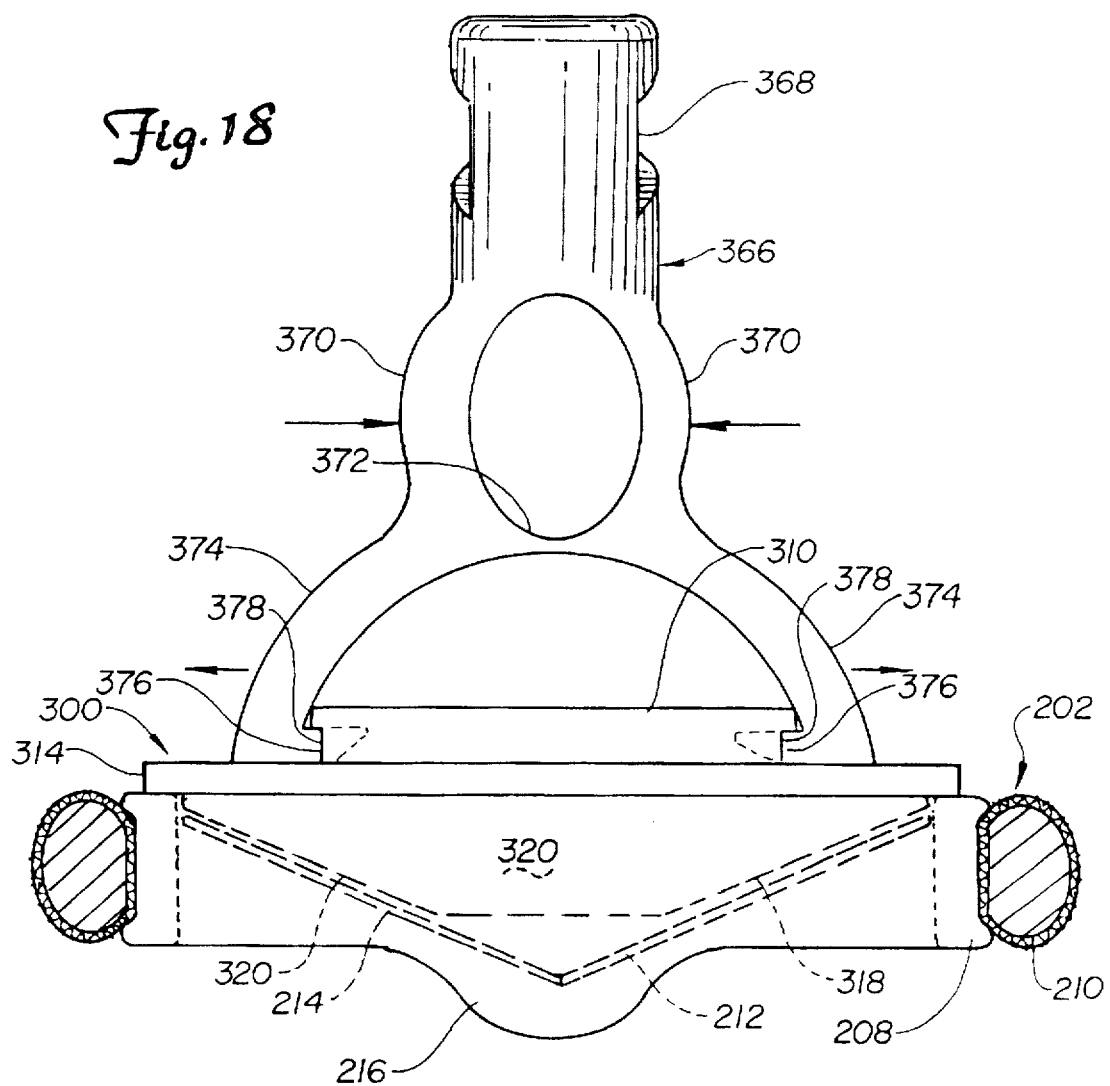
FIG. 18 is a plan view of a hanger adapted for engaging the holder of FIGS. 14, 16 and 17.

FIG. 18 is a plan view of hanger 366 adapted for carrying holder 300, or one or more of the holder embodiments shown herein, and attachment to packaging (not shown). For illustrative purposes, valve 202 is shown in cross section. Hanger 366 includes notches 368 adapted for attachment to packaging (not shown), release points 370, pivot 372 and legs 374. Each leg 374 includes tab 376 at its distal end which is adapted to be received in openings 378 of holder 300. Application of pressure to points 370 in the direction shown by the arrows causes legs 374 to spread apart outwardly thereby releasing tabs 376 from openings 378 in holder 300. In one embodiment, a locking member such as a bar extending between points 370 prevents holder 300 from inadvertently being released from hanger 366 by application of pressure to points 370. Such a locking member can be removed or cut at the appropriate time to allow release of holder 300.

Figure 19:
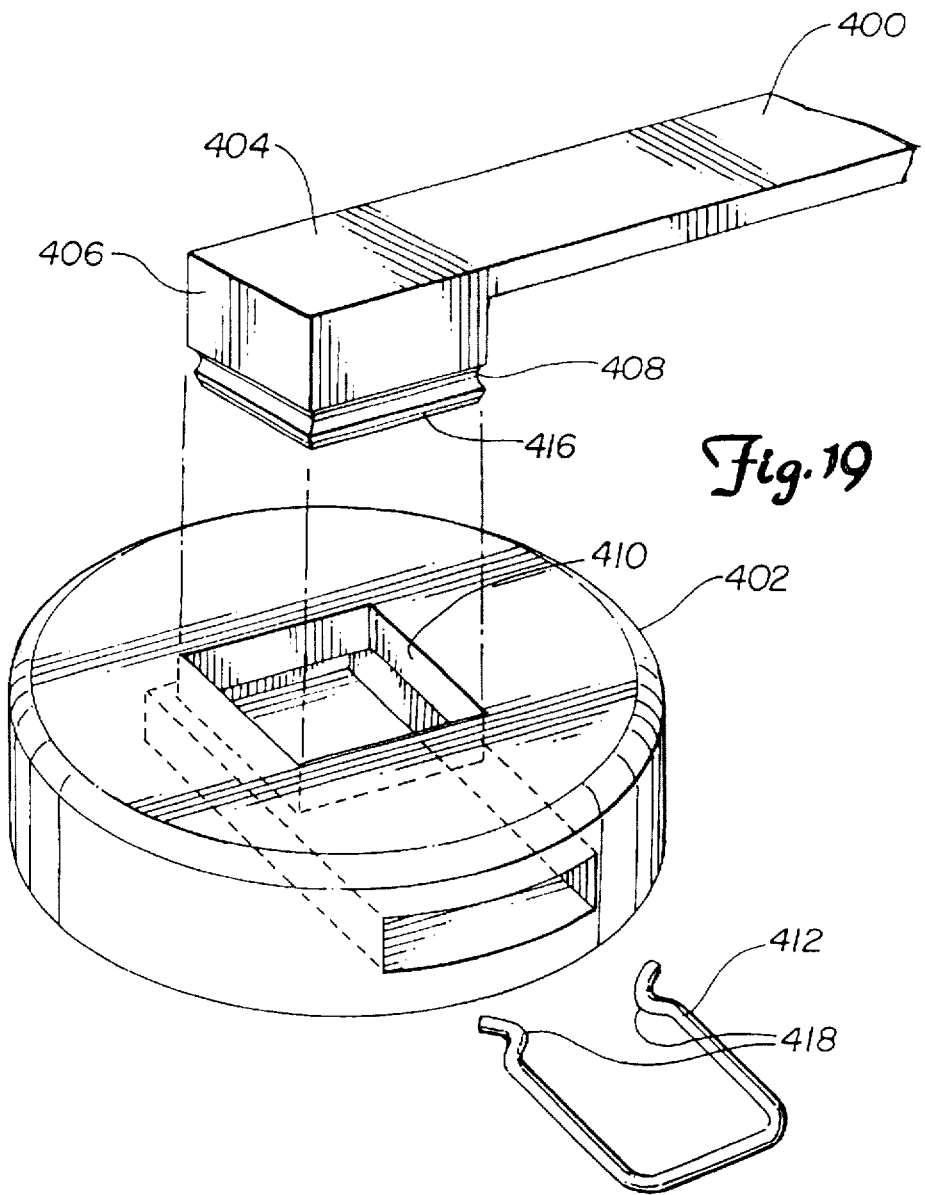
FIG. 19 is an exploded perspective view showing attachment of a handle to a holder in accordance with another embodiment.
Figure 20:
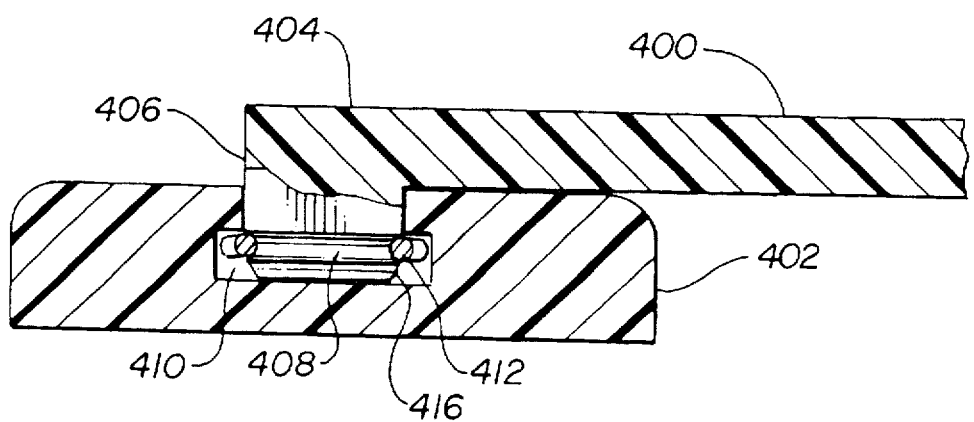
FIG. 20 is a cross-sectional view of the holder and handle of FIG. 19.

FIGS. 19 and 20 are perspective and cross-sectional views, respectively, of another embodiment for attaching a handle 400 to a valve holder shown generally at 402. Distal end 404 of handle 400 includes attachment portion 406 having groove 408 formed therein. Holder 402 includes opening 410 which carries spring loaded locking clip 412 which is typically any material with sufficient spring properties, such as metals or polymers, such as a formed spring material, shaped memory material, a metal or a polymer. Locking clip 412 is held in holder 402. Attachment portion 406 is urged downward into opening 410. Beveled (or chamfered) section 416 causes tips 418 of clip 412 to be spread apart in an outward direction. Once locking portion 406 has fully entered opening 410, tips 418 lock into groove 408 thereby securing handle 400 to holder 402. Handle 400 is removed by simply pulling it out of opening 410.

Figure 21:
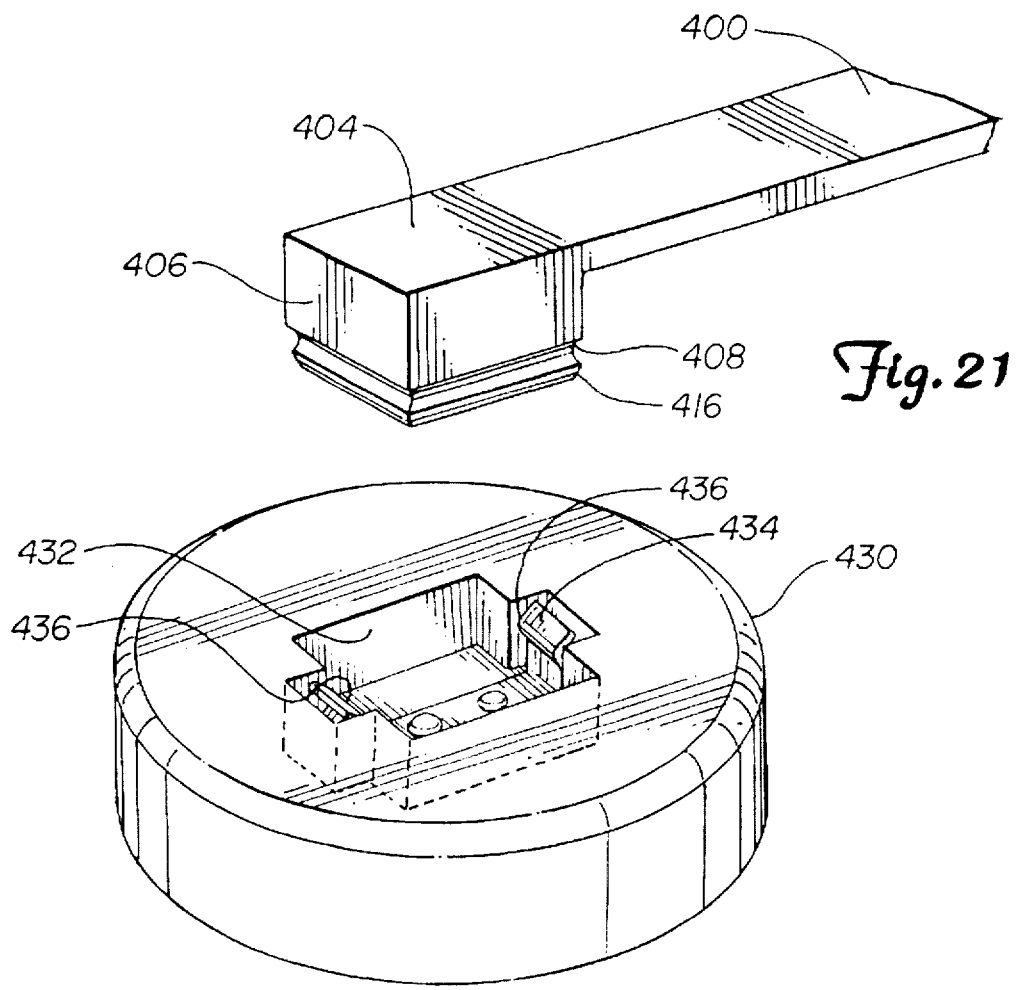
FIG. 21 is an exploded perspective view showing attachment of a handle to a holder in accordance with another embodiment.
Figure 22:
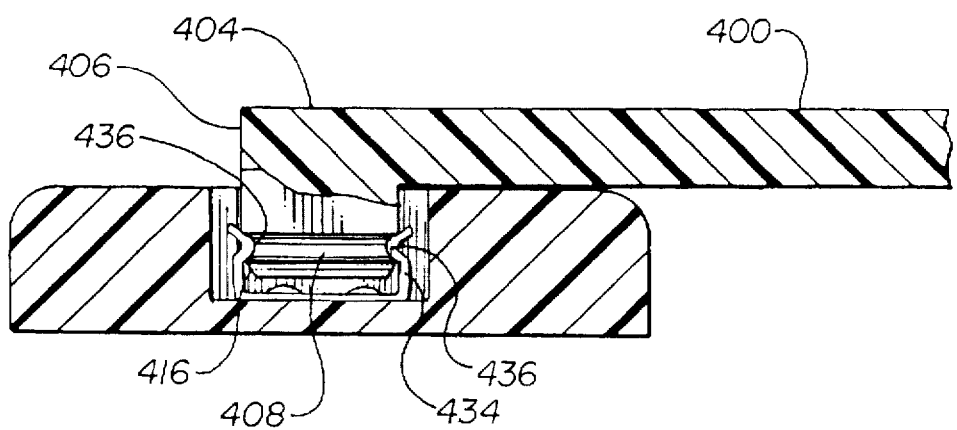
FIG. 22 is a cross-sectional view of the embodiment of FIG. 21.

FIGS. 21 and 22 are perspective and cross-sectional views, respectively, of another embodiment of the invention for attaching handle 400 to low profile valve holder shown generally at 430. Holder 430 includes opening 432 for receiving attachment portion 406. Opening 432 carries attachment clip 434 having ridges 436 adapted for engaging groove 408. Handle 400 is removed by simply pulling it from opening 432.

Figure 23:
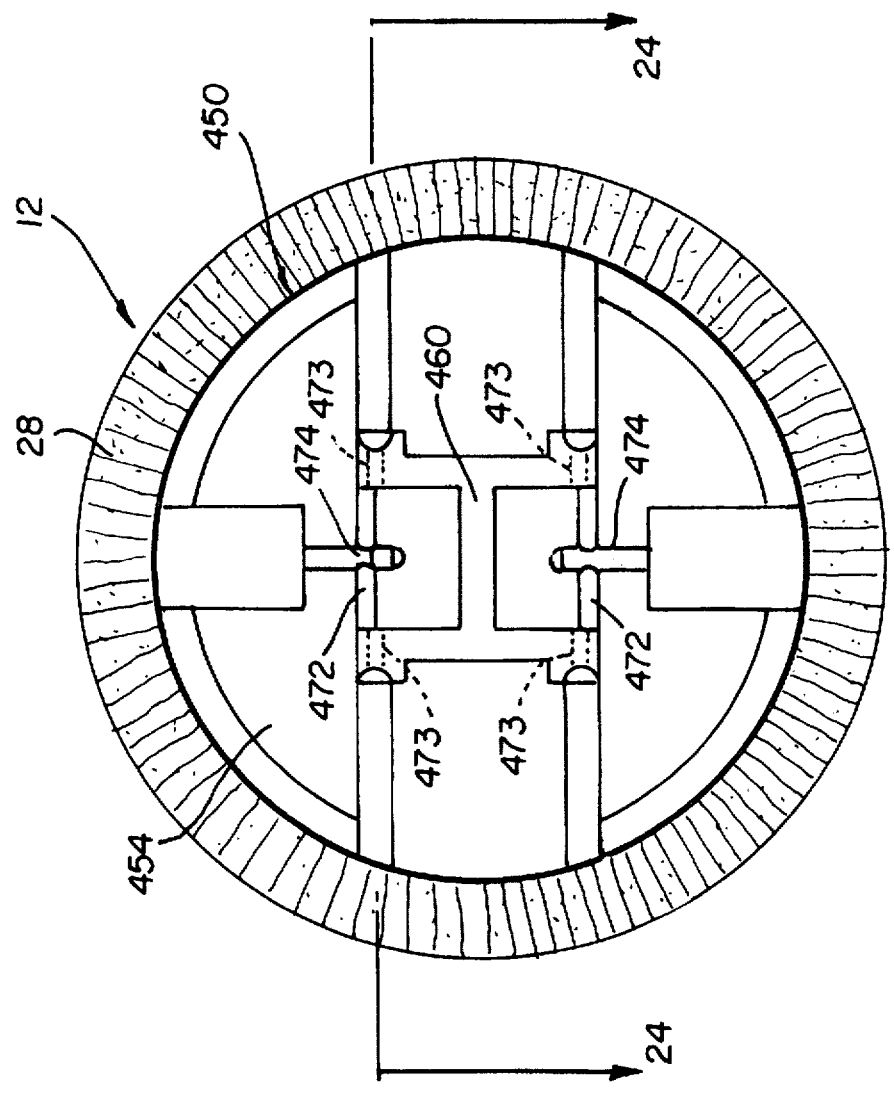
FIG. 23 is a top plan view of a holder in accordance with another embodiment.
Figure 24:
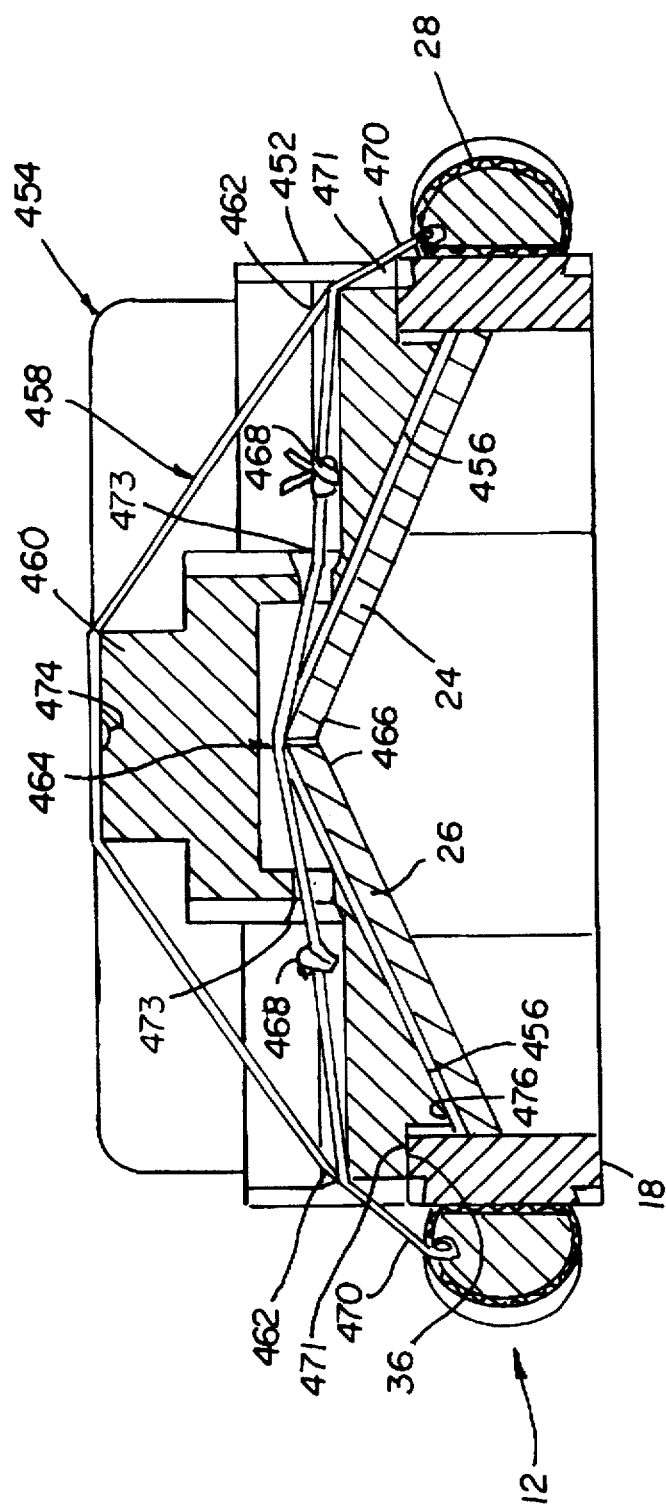
FIG. 24 is a side cross sectional view of the embodiment shown in FIG. 23 taken along the line labeled 24—24.
Figure 25:
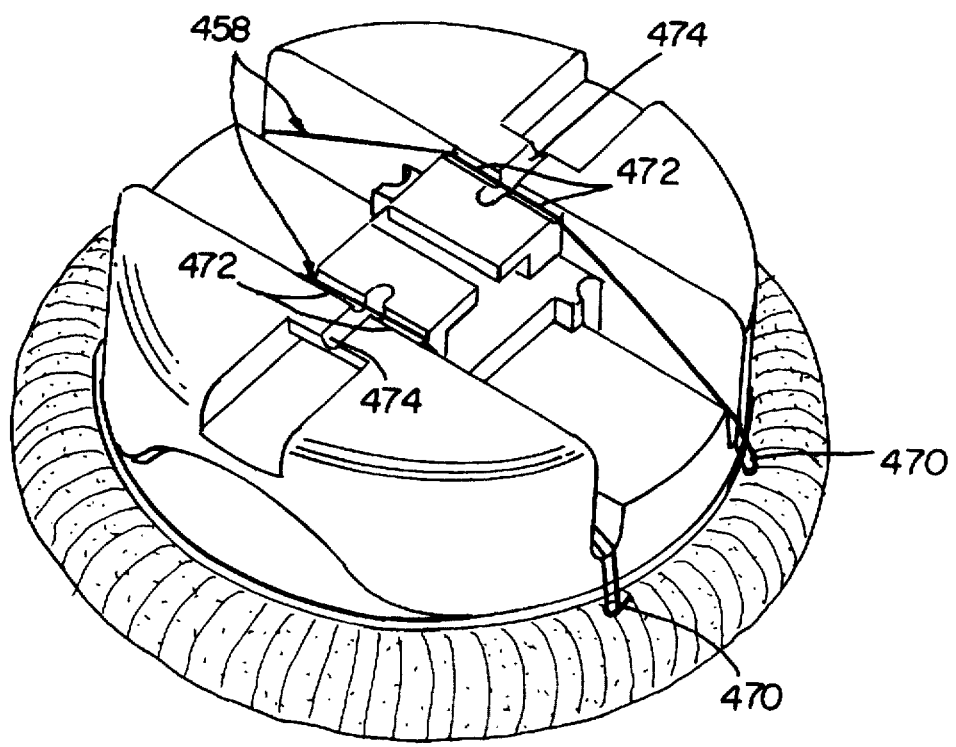
FIG. 25 is a perspective view of the embodiment shown in FIG. 23.

FIG. 23 is a top plan view, FIG. 24 is a side cross sectional view, and FIG. 25 is a perspective view of a heart valve prosthesis holder 450 in accordance with another embodiment. Holder 450 is shown coupled to heart valve prosthesis 12. Holder 450 includes holder body 452, holder proximal surface 454 and holder distal surfaces 456 which are adjacent occluders 24 and 26. It has been discovered that a compliant material between holder 450 and valve 12 is well suited for maintaining occluders 24 and 26 in a substantially closed position as shown in FIG. 24. The compliant material is preferably soft, is capable of pushing against occluders 24 and 26 to maintain them in the closed position, and does not require precision manufacturing of the surface which engage occluders 24, 26. Compliant material may optionally be attached to holder 450. In the embodiment of holder 450, a suture 458 provides such engagement to maintain occluders 24 and 26 in a closed position.

Suture 458 extends over an elevated suture tensioning extension 460, through suture openings 462 and across the body 452 of holder 450. Suture 458 provides an occluder engaging portion 464 which is positioned adjacent upstream edges 466 of occluders 24 and 26. In another embodiment, separate sutures may be used. Suture 458 is secured with knots 468. In one embodiment, attachment portions 470 of suture 458 extend through suture cuff 28 to attach holder 450 to valve 12. In an alternative embodiment, suture adjacent upstream edges 466 of occluders 24 and 26 may be independent of suture 458 which attaches valve to holder. Suture 458 secures valve 12 to prosthesis holder 450 such that distal surface 471 of holder body 452 is held in abutting contact with radial lip 36 of orifice 18. An internal extension 476 extends into the orifice of valve 12 and generally conforms to the internal surface of orifice 18. A substantially cylindrical or annular extension 476 helps align holder 450 to valve 12 to maintain holder 450 and valve 12 in a coaxial position with each other. As shown in FIG. 23, suture tensioning extension 460 includes slots 472 for carrying suture 458. Extension 460 also provides suture cutting slots 474 which are suitable for receiving a scalpel to cut suture 458 and thereby release valve 12 from holder 450. Small openings 473 in slots 474 prevent knots 468 from being withdrawn from holder 450 such that sutures 458 remain attached to holder 450 even after they are cut. In the embodiment of FIGS. 23 and 24, distal surfaces 456 do not contact occluders 24 and 26. Although the embodiment of FIGS. 23 and 24 provides a suture to maintain occluders 24 and 26 in a substantially closed position, other techniques may also be employed. For example, compliant materials may be a plug or a pad made from polymers including polytetrafluoroethylene (PTFE), polymeric foams such as polyolefins elastomers such as silicone, a springs or woven fabrics such as polyester may be attached to holder 450 to maintain occluders 24 and 26 in the closed position. This allows occluders 24 and 26 to be protected within annulus 18 during implantation.

In general, the materials used herein are materials suited for the biomedical industry. For example, the holder can be made of a polymer such as polysulfone, known under the trade name of Udel®, or other similar biocompatible durable material, and is suitable for forming by injection molding or machining techniques. Typical materials for the handle include stainless steel or cobalt alloys. In the embodiment of handle 330 shown in FIG. 15, a suitable spring material is desirable such as cobalt chrome or cobalt nickel alloys or stainless steel. The embodiments shown in FIGS. 19 through 25 allow for ease of disengagement of the handle from the holder following removal of the holder from the patient. Additionally, all designs tend to allow easy attachment of the handle to the holder during surgery while maintaining the sterile condition of the pieces. Injection molding techniques are well suited for fabricating the low profile holder set forth herein. A suitable distance between an occluder and an occluder engaging surface is maintained so as to not apply excessive pressure to the occluders during transportation or use of the valve while attached to the low profile holder. This stabilizes the occluder without substantial contact to the occluder which could damage the occluder. Furthermore, the holder set forth herein provides a pivot guard to prevent the handle from contacting the valve during use. One aspect of the invention includes placing the handle in close proximity with the valve and in a plane parallel with the valve annulus to reduce the height of the valve/holder assembly. Where appropriate, these designs may be used for either mitral or aortic valves.

The invention as set forth herein securely attaches the holder to the valve and the valve to the handle or hanger as one integral piece until the sutures are cut. The low profile design allows easy and safe manipulation of the valve in a surgical environment and during implantation. Easy engagement (and disengagement) of the holder and handle assembly is provided which has advantages including speed, ease, safety and effectiveness in a surgical environment. The integral packaging allows the entire assembly to be sterilized as a unit. The various elements are provided for easy manufacture using injection molding techniques. Protection of the occluders within the valve orifice is maintained and the low profile allows minimally invasive surgical techniques. The slots, grooves and openings in the valve holders which receive sutures position and protect sutures from inadvertent cutting and aid in minimizing the holder-valve assembly profile since the suture does not protrude above the holder.

Although the present invention has been described with reference to preferred embodiments, workers skilled in the art will recognize that changes may be made in form and detail without departing from the spirit and scope of the invention.

What is claimed is:

1. A holder for holding a heart valve prosthesis during implantation in a patient, the heart valve having an annulus and at least one occluder carried therein moveable between an open position allowing flow through the annulus and a substantially closed position substantially blocking flow through the annulus, the holder comprising:

a holder body generally conforming to the annulus of the heart valve prosthesis;

an annular extension protruding from the holder body and adapted to protrude into the annulus of the heart valve prosthesis, at least a portion of the extension adapted to generally conform to a portion of an inner surface of the heart valve prosthesis;

means coupled to the holder body for attaching the holder body to the heart valve prosthesis, wherein the means for attaching comprises an attachment suture; and an occluder engaging compliant member adjacent the holder body adapted to engage the occluder, the member positioned to contact the occluder when the holder body is attached to the heart valve prosthesis whereby the occluder is maintained in the substantially closed position and substantially protected by the annulus of the heart valve prosthesis, wherein the occluder engaging compliant member comprises an occluder engaging suture which is adapted to extend adjacent the annulus of the heart valve prosthesis and is adapted to contact the occluder to maintain the occluder in the substantially closed position.

2. The holder of claim 1 wherein the means for attaching comprises an attachment suture.

3. The holder of claim 1 wherein the engaging suture is adapted to couple the holder to the heart valve prosthesis and thereby provide the means for attaching.

4. The holder of claim 1 wherein the holder body includes a suture opening formed therein and the occluder engaging suture extends through the suture opening.

5. The holder of claim 4 wherein the suture is knotted within the holder body.

6. The holder of claim 5 wherein the knot attaches the suture to the holder body whereby the suture remains coupled to the holder body if the suture is severed.

7. The holder of claim 1 including an elevated suture tensioning extension extending in a direction away from the holder body, wherein the occluder engaging suture extends over the suture tensioning extension which provides tension on the suture to maintain the occluder in the closed position when the holder body is attached to the heart valve prosthesis.

8. The holder of claim 7 wherein the elevated suture extension includes a top surface having a suture guide formed therein for receiving the occluder engaging suture.

9. The holder of claim 1 wherein the heart valve prosthesis includes two occluders moveable between open and closed positions and the occluder engaging member is adapted to maintain both occluders in substantially closed positions when the holder body is attached to the heart valve prosthesis.

10. The holder of claim 1 including a second occluder engaging suture.

11. A holder for holding a heart valve prosthesis during implantation in a patient, the heart valve having an annulus and at least one occluder carried therein moveable between an open position allowing flow through the annulus and a substantially closed position substantially blocking flow through the annulus, the holder comprising:

a holder body generally conforming to the annulus of the heart valve prosthesis;

means coupled to the holder body for attaching the holder body to the heart valve prosthesis; and an occluder engaging suture adjacent the holder body adapted to engage the occluder, the suture extending across the holder body and adapted to be positioned in the annulus of the heart valve prosthesis to thereby contact the occluder when the holder body is attached to the heart valve prosthesis whereby the occluder is maintained in the substantially closed position and substantially protected by the annulus of the heart valve prosthesis.

12. The holder of claim 11 wherein the means for attaching comprises an attachment suture.

13. The holder of claim 11 wherein the engaging suture is adapted to couple the holder to the heart valve prosthesis and thereby provide the means for attaching.

14. The holder of claim 11 wherein the holder body includes a suture opening formed therein and the occluder engaging suture extends through the suture opening.

15. The holder of claim 14 wherein the suture is knotted within the holder body.

16. The holder of claim 15 wherein the knot attaches the suture to the holder body whereby the suture remains coupled to the holder body if the suture is severed.

17. The holder of claim 11 including an elevated suture tensioning extension extending in a direction away from the holder body, wherein the occluder engaging suture extends over the suture tensioning extension which provides tension on the suture to maintain the occluder in the closed position when the holder body is attached to the heart valve prosthesis.

18. The holder of claim 17 wherein the elevated suture extension includes a top surface having a suture guide formed therein for receiving the occluder engaging suture.

19. The holder of claim 11 wherein the heart valve prosthesis includes two occluders moveable between open and closed positions and the occluder engaging suture is adapted to maintain both occluders in substantially closed positions when the holder body is attached to the heart valve prosthesis.

20. The holder of claim 11 including a second occluder engaging suture.

21. The holder of claim 11 including an annular extension protruding from the holder body and adapted to protrude into the annulus of the heart valve prosthesis, at least a portion of the extension adapted to conform to a portion of an inner surface of the heart valve prosthesis.

* * * * *

UNITED STATES PATENT AND TRADEMARK OFFICE
CERTIFICATE OF CORRECTION

Page 1 of 2

PATENT NO. : 5,735,894
DATED : April 7, 1998
INVENTOR(S) : Kurt D. Krueger et al.

It is certified that error appears in the above-identified patent and that said Letters Patent is hereby corrected as shown below:

Under [56] References Cited
U.S. PATENT DOCUMENTS

Insert --

| | | |
|---|---|---|
| 3,828,787 | 8/1974 | Anderson et al.....128/303 |
| 4,655,218 | 4/1987 | Kulik et al........128/321 |
| 4,932,965 | 6/1990 | Phillips...........623/2 |
| 5,236,450 | 8/1993 | Scott..............623/2 |
| 5,370,685 | 12/1994 | Stevens............623/2 |
| 5,403,305 | 4/1995 | Sauter et al.......606/1 |
| 5,531,785 | 7/1996 | Love et al.........623/2 |
| 5,571,215 | 11/1996 | Sterman et al......623/66 |
| 5,628,789 | 5/1997 | Vanney et al.......623/2-- |

UNITED STATES PATENT AND TRADEMARK OFFICE
CERTIFICATE OF CORRECTION

PATENT NO. : 5,735,894
DATED : April 7, 1998
INVENTOR(S) : Kurt D. Krueger et al.

It is certified that error appears in the above-identified patent and that said Letters Patent is hereby corrected as shown below:

Under FOREIGN PATENT DOCUMENTS

Insert --
| | | |
|---|---|---|
| 1690738 | 11/1991 | U.S.S.R. |
| WO 91/17720 | 11/1991 | WIPO |
| WO 94/18881 | 9/1994 | WIPO |
| WO 95/15715 | 6/1995 | WIPO |
| WO 95/17139 | 6/1995 | WIPO-- |

Signed and Sealed this

First Day of December, 1998

Attest:

BRUCE LEHMAN

*Attesting Officer*   Commissioner of Patents and Trademarks